(12) United States Patent
Chong

(10) Patent No.: US 8,027,085 B2
(45) Date of Patent: Sep. 27, 2011

(54) MICROSCOPE WITH CENTERED ILLUMINATION

(75) Inventor: Soon Haw Chong, Widnau (CH)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 706 days.

(21) Appl. No.: 12/145,391

(22) Filed: Jun. 24, 2008

(65) Prior Publication Data

US 2009/0021827 A1  Jan. 22, 2009

(30) Foreign Application Priority Data

Jun. 28, 2007 (DE) .................. 10 2007 029 896

(51) Int. Cl.
*G02B 21/06* (2006.01)
(52) U.S. Cl. .................. 359/385; 359/388; 359/389
(58) Field of Classification Search .......... 359/385–389
See application file for complete search history.

(56) References Cited

U.S. PATENT DOCUMENTS

| | | | |
|---|---|---|---|
| 5,748,367 A * | 5/1998 | Lucke et al. .......... | 359/385 |
| 6,473,229 B2 | 10/2002 | Nakamura | |
| 6,972,900 B2 * | 12/2005 | Sander .............. | 359/372 |
| 7,102,818 B2 | 9/2006 | Sander | |
| 7,924,502 B2 * | 4/2011 | Weiler et al. ......... | 359/385 |
| 2001/0010592 A1 | 8/2001 | Nakamura | |
| 2003/0048530 A1 | 3/2003 | Sander | |
| 2004/0057108 A1 | 3/2004 | Namii | |

FOREIGN PATENT DOCUMENTS

| | | |
|---|---|---|
| DE | 195 23 712 C2 | 1/1996 |
| DE | 195 37 868 B4 | 4/1996 |
| DE | 195 37 969 A1 | 4/1997 |
| DE | 10144062 | 3/2003 |
| EP | 0321586 | 6/1989 |
| EP | 1 424 582 B1 | 6/2004 |
| EP | 1424582 | 6/2004 |

OTHER PUBLICATIONS

Office Action issued by the United States Patent and Trademark Office for U.S. Appl. No. 12/145,863 dated Jun. 12, 2009.
Office Action issued by the United States Patent and Trademark Office for U.S. Appl. No. 12/145,863 dated Jan. 12, 2010.
Office Action issued by the United States Patent and Trademark Office for U.S. Appl. No. 12/145,863 dated Mar. 18, 2010.
Office Action issued by the United States Patent and Trademark Office for U.S. Appl. No. 12/145,863 dated Apr. 21, 2010.
Office Action issued by the United States Patent and Trademark Office for U.S. Appl. No. 12/145,868 dated Jun. 8, 2009.
Office Action issued by the United States Patent and Trademark Office for U.S. Appl. No. 12/145,868 dated Mar. 31, 2010.
Office Action issued by the United States Patent and Trademark Office for U.S. Appl. No. 12/145,863 dated Oct. 13, 2010.

* cited by examiner

*Primary Examiner* — Joshua L Pritchett
(74) *Attorney, Agent, or Firm* — Schlee IP International, P.C.; Alexander R. Schlee

(57) ABSTRACT

A microscope comprising a main objective having a lens assembly movable in the direction of the optical axis of the main objective for focal length change and comprising an illuminating unit with illumination deflector elements for deflecting an illuminating beam path for generating an illuminating beam path directed onto an object plane. The position of the illumination deflector elements is adjustable dependent on a focal length change of the main objective for centering the illumination, and the illumination deflector elements are designed as at least partly integrated into the movable lens assembly of the main objective. For this purpose, in particular a part of the lens surface of the movable lens assembly can be made reflective.

19 Claims, 5 Drawing Sheets

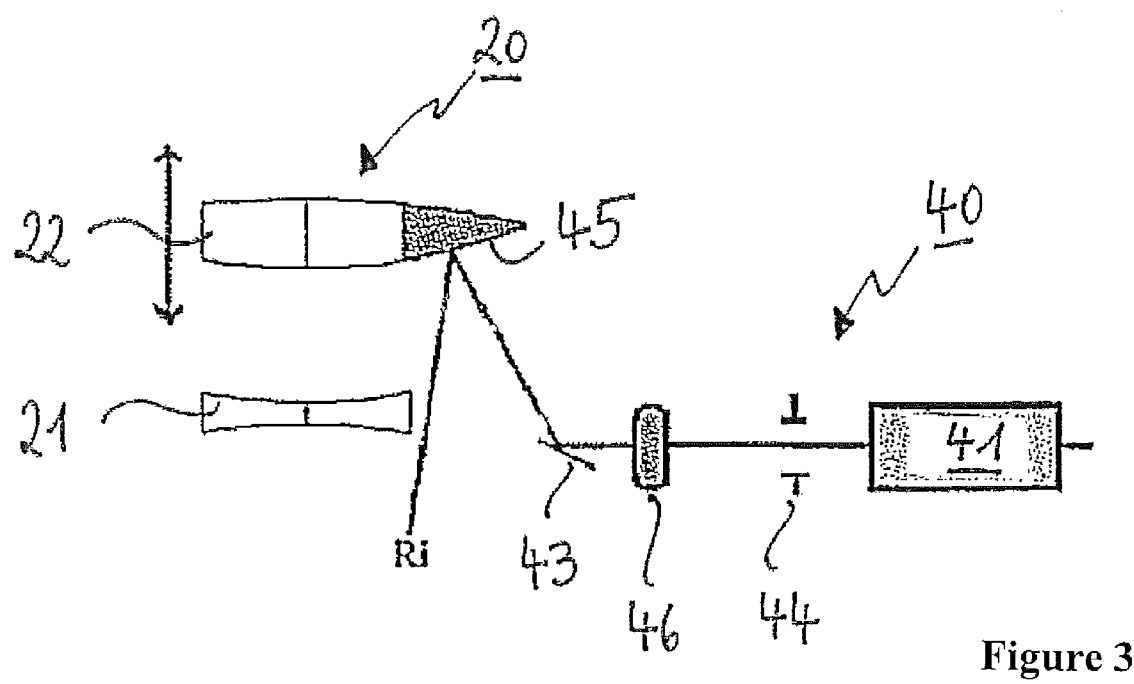
Figure 3

ns with "lying" zoom system reference is explicitly made to the mentioned European patent specification.

MICROSCOPE WITH CENTERED ILLUMINATION

This application claims the priority of the German patent application DE 10 2007 029 896.1 having a filing date of Jun. 28, 2007, the entire content of which is herewith incorporated by reference.

BACKGROUND OF THE INVENTION

The present invention relates to a microscope comprising a main objective having a lens assembly movable in the direction of the optical axis of the main objective for focal length variation and comprising an illuminating unit with illumination deflector means for deflecting an illuminating beam path for generating an illuminating beam path that is directed onto an object plane, the position of the illumination deflector means being adjustable dependent on a focal length variation of the main objective for centering the illumination.

Microscopes of this type are known from DE 195 23 712 C2 and DE 195 37 868 B4. In the first-mentioned DE 195 23 712 C2 a stereomicroscope comprising a main objective with variable focal length, a downstream zoom system and a binocular tube as well as an illuminating unit arranged adjacent to the main objective is disclosed. The main objective comprises a fixed and a movable lens for varying the focal length and the intercept length of the main objective. The fixed, negative lens of the main objective is arranged towards the object plane, the movable, positive lens is arranged behind it (facing away from the object plane). A movement of the movable lens in the direction away from the object plane results in a reduction of the focal length of the main objective. For an optimal illumination of the vertically shifting object plane, it is suggested in this document to adjust the position of an illumination deflector element dependent on a focal length variation of the main objective for centering the illumination. This is done in that the prism lens used as an illumination deflector element is pivoted such that the illuminating beam path tracks the shifted object plane. For this purpose, the prism lens is pivotally mounted about an axis which is perpendicular to a plane that is spanned by the vertical optical axis of the main objective and the illuminating beam path which is incident substantially horizontally inclined on the prism lens. As a result thereof, for all positions of the movable lens of the main objective facing away from the object a focusing of the illuminating light on the respective focal point of the main objective can be guaranteed.

The coupling of the rotary movement of the illumination deflector element with the linear (vertical) movement of the lens of the main objective facing away from the object, as suggested in this document, requires very sensitive rotary movements of the illumination deflector element in relation to the movement of the lens and makes high demands on the mechanical coupling which is designed with a high constructional expense in this document. Any disturbances will be directly visible for the user (particularly given high magnifications). Further, the size of the surface of the deflector element turns out to be disadvantageous, as it has to be sufficiently large in order to cover the entire illuminating pencil even when the illumination deflector element is tilted. Mirrors or the mentioned prism lenses can be used as illumination deflector elements. When mirrors are used, an enlargement of the reflecting surface will result in the additional disadvantage of an increased required thickness of the reflecting surface. Thus, altogether the required space and the height of the weight to be moved are increased.

In the mentioned DE 195 37 868 B4, an illuminating device for a stereomicroscope comprising an objective with a variable image-forming intercept length is disclosed, an illumination intercept length variation being possible via an optical system that is separate from the viewing optical system. Means for coupling the intercept lengths mentioned are disclosed, which means effect that the illumination intercept length and the image-forming intercept length correspond to one another. Further, means for coupling are provided which guarantee that the angular position of a deflector element of the illuminating device is varied such dependent on the respective image-forming intercept length and illumination intercept length that there is always a centered illumination of the viewed field of view. Since, here too, for centering the illumination rotary movements of the illumination deflector elements are performed, here, once again, the disadvantages mentioned occur.

A basically different possibility of illumination centering results when the illumination is guided through the main objective of the microscope. This solution is implemented in the surgical microscope models M520 and M525 of the applicant. Here, the illumination deflector element directs the illuminating beam path to and through the main objective having variable focal length so that the illumination is always centered on the focus.

The microscopes mentioned up to now use vertical zoom systems, i.e. the longitudinal axis of the zoom system lies parallel to the optical axis of the main objective. If, in addition, the illumination is fed into the main objective from above, there will be a high space requirement in vertical direction resulting in microscopes having a relative high overall height in the vertical direction. This is disadvantageous for ergonomic reasons since the distance between the eyepiece and the main objective is increased.

For solving the last-mentioned problem, a stereomicroscope structure has been suggested in the document EP 1 424 582 B1, in which a "lying" zoom system, i.e. a zoom system having its longitudinal axis arranged horizontally, is realized. For this purpose, there is arranged between the main objective and the zoom system a deflector element which deflects the viewing beam path from a substantially vertical direction into a substantially horizontal direction and feeds the same into the zoom system arranged in a first horizontal plane. By means of further deflector elements the viewing beam path exiting the zoom system is deflected into a second horizontal plane which extends substantially parallel to the first horizontal plane and in which optical add-on components are arranged. With respect to details on the structure and the mode of functioning of such a stereomicroscope with "lying" zoom system reference is explicitly made to the mentioned European patent specification.

In this stereomicroscope, the illuminating unit is arranged substantially adjacent to the main objective und below the zoom system, the illuminating beam path being guided outside the main objective. Instead of an illumination centering, it can be ensured by means of a sufficiently large illuminated field that the visual field is always illuminated given a focal length variation of the main objective. Such a generously designed illuminated field requires a correspondingly largely designed illuminating aperture and thus illuminating unit, which in turn has a negative effect on the ergonomics of the microscope. A further disadvantage in this connection is that the homogeneity of the illumination (intensity in the illuminated field) cannot be the same for all positions of the multi-focus (variable focus lens). Only another section of the entire available illuminated field is used.

SUMMARY OF THE INVENTION

The present invention is to be particularly suitable for illumination centering in a microscope structure making use of "lying" zoom systems.

The problem to be solved by the present invention is to realize in a technically easy way a centering of the illumination given a focal length variation of the main objective of the microscope.

The inventive microscope comprises a main objective having a variable focal length, for which a lens assembly movable in the direction of the optical axis of the main objective is provided. In this application, the terms multi-focus or variable focus lens shall refer to such a main objective of variable focal length. Without restricting the generality, it is assumed in the following that this main objective comprises a fixed part and a movable part, each of these parts including a lens assembly. A lens assembly can comprise a single lens or a combination of lenses. The variable focus lens can, for example, be constructed such that the lower, object-facing part is fixed, and the upper part, facing away from the object, is movably designed. By using such a variable focus lens different object planes can be focused in a certain area.

The inventive microscope further comprises an illuminating unit with illumination deflector means for deflecting an illuminating beam path for generating an illuminating beam path directed onto an object plane, the position of the illumination deflector means being adjustable dependent on a focal length variation of the main objective for centering the illumination. Without restricting the generality, it is assumed, as far as not stated otherwise, that the illuminating unit at first generates a horizontally directed illuminating beam path, the axis of which is substantially perpendicular (or inclined) to the optical axis of the main objective. The illumination deflector means direct this illuminating beam path in the direction of the object plane onto the focus of the main objective. The optical axis of the main objective is in this case perpendicular to the object plane.

According to the invention, the illumination deflector means are at least in part integrated into the movable lens assembly of the main objective and thus change their position dependent on a focal length variation of the main objective. In this way, it is made possible that the illumination centering directly and inevitably follows a focal length variation. The coupling of the focal length variation with a rotary or tilting movement of an illumination deflector element known up to now and requiring a high technical expense can thus be omitted.

The part of the illumination deflector means integrated into the movable lens assembly of the main objective can, for example, be a deflector element such as a deflecting mirror or deflecting prism, which is firmly connected to the movable lens assembly. On the other hand, the mentioned part of the illumination deflector means can likewise be a lens surface of the movable lens assembly of the main objective which surface is at least partially made reflective. In the following, the invention shall be explained on the basis of these two alternatives without restricting the generality.

The deflector element firmly connected to the movable lens assembly of the main objective can have a plane or a spherical reflecting surface. A spherical reflecting surface has beam-changing properties which can advantageously be used. A deflector element having a freeform reflecting surface can also be used for this purpose.

A particularly preferred embodiment of the invention comprises the already mentioned possibility of making a lens surface of the movable lens assembly of the main objective at least partially reflective. The lens surface area which has been made reflective can have the same or a different lens or surface curvature as the non-reflecting surface. Such a different lens curvature can, for example, be realized by means of a lens cemented thereto. This cemented lens does, for example, not change the (image-forming) lens curvature predetermined for the viewing beam path, however has a lens curvature in the reflecting surface area that is correspondingly adapted for illumination centering. The same effect can also be achieved with a single lens having a freeform surface. The mentioned-areas (area for image-forming and area for reflection) on the lens then have a continuous transition.

A lens surface which has partially been made reflective is usually not flat but, as a result of the surface curvature, has a positive or negative refractive power, i.e. a focusing or defocusing effect. Therefore, in this case, the reflecting lens surface area can be used like an additional lens for the illuminating unit.

In all of the cases mentioned it can be expedient when the illumination deflector means have a further deflector element which optically interacts with the part of the illumination deflector means integrated into the lens assembly of the main objective, in particular is arranged upstream of this integrated part. As a result thereof, the angle of incidence of the illuminating beam path onto the integrated part of the illumination deflector means, i.e. for example onto the deflector element or onto the reflecting lens surface, can be optimally set in a simple and reliable way in that the illuminating beam path is first directed onto the further illumination deflector element before it is directed from there onto the part of the illumination deflector means integrated into the lens assembly, from where the illuminating beam path is in turn directed in the direction of the object plane. It turned out that the mentioned further deflector element can be static, i.e. does not have to be pivotally or tiltably mounted. The centering of the illumination, i.e. the required lateral shift of the illuminated field given a focal length variation of the main objective and thus a variation in the field of view can be simply accomplished in that the illuminating beam path is reflected on the movable lens assembly of the main objective.

For making a lens surface of the movable lens assembly of the main objective partially reflective, the major part of the lens surface area used by the viewing beam path(s) can, for example, be coated with a non-reflective material and the area used for reflection, which area preferably lies in the periphery of the lens, can be coated with a reflective material.

Since single lenses as well as many-membered lens groups have different, in particular differently curved lens surfaces, a suitable lens area for the application of a reflective material can be chosen dependent on the structure of the main objective and of the illuminating unit.

In principle, two different possibilities for varying the focal length of a main objective can be distinguished which shall be explained in more detail in the following. Of course, many different structures of variable focus lenses or multi-focus lenses are known, and the person skilled in the art will usually be able to readily apply the present invention onto the respective specific structure of the variable focus lens. This shall be illustrated on the basis of the two basic possibilities mentioned:

The variable focus lens (multi-focus lens) can be composed of two lens assemblies having focal lengths with different signs, which lens assemblies are mounted such that they can be moved relative to one another. Given this structure, an increase in the distance between the two lens assemblies results in a reduction of the working distance, the focal length and the intercept length of the main objective.

As a second possibility, two lens assemblies having focal lengths with positive signs can be used in a variable focus lens (multi-focus lens), which lens assemblies are movably mounted relative to one another. In this case, an increase in the distance between the two lens assemblies results in an increase in the working distance, the focal length and the intercept length of the main objective.

Without restricting the generality, it is assumed in the following that in both possibilities mentioned, each time the lens assembly having positive refractive power (focal length with positive sign) is movably mounted. A lens assembly having a positive focal length, i.e. for example a collective lens, has with respect to an incident beam of light at first a convex surface curvature (positive radius of curvature) and on the light exit side a concave lens surface (negative radius of curvature). It has proven advantageous and sufficient to, dependent on the mentioned possibility of focal length variation, either make the convex or the concave lens surface of the movable lens assembly having a positive focal length partially reflective.

Given the first-mentioned possibility of lens assemblies having focal lengths with different signs preferably a part of the convex lens surface of this lens assembly is made reflective. The convex lens surface here represents the surface which faces the incident illuminating beam path. In the second-mentioned case of lens assemblies having focal lengths with positive signs it is advantageous to have a concave lens surface of the movable lens assembly partially made reflective. Further details with regard thereto can be taken from the embodiments discussed below.

It can be useful when the lens curvature on the reflecting surface of the lens assembly is different from the lens curvature on the non-reflecting surface of the lens assembly. Should, for example, the lens curvature present not be sufficient in order to deflect the illuminating beam path in a sufficient way given a focal length variation of the main objective, then, for example, a reflecting surface which has a higher curvature, for example in the form of an additional lens cemented thereto, can be mounted to the moveable lens assembly. Again, reference is made to the possibility of a lens having a freeform surface.

The illuminating beam path reflected on the movable lens assembly can afterwards be directed onto the object plane outside the main objective, but can also be directed onto this object plane via the remaining part of the main objective. This remaining part can, for example, be a lens assembly with positive or negative refractive power facing the object plane. This part of the main objective can thus be suitably used as a further lens of the illuminating unit.

It can be expedient, in particular when the integrated part of the illumination deflector means concerned is a deflector element (deflecting mirror) firmly connected to the movable lens assembly, and in particular when this part concerned is a plane mirror, to design at least part of the illuminating unit such that the illuminating beam path generated by the illuminating unit follows a movement of this integrated part of the illumination deflector means or, respectively, of the deflector element or respectively of the plane mirror. The change in angle required for centering the illumination given the reflection of the illuminating beam path on the movable lens assembly is in this case then not only caused by the movement of the lens assembly itself but, in addition, by a tracking of the illuminating beam path.

For this purpose, it is useful to mount at least part of the illuminating unit tiltably about an axis which is substantially perpendicular to a plane spanned by the optical axis of the main objective and the axis of the illuminating beam path. By tilting this part of the illuminating unit the illuminating beam path can each time be tracked or guided in the direction of the position of the lens assembly. Given a tracking of the illuminating beam path, the possibly available additional deflecting mirror (further deflector element) can usually be done without.

Suitable illuminating units to be used in the present microscopes are known per se. Light can be supplied to the illuminating unit via a light guide. For example halogen, xenon or LED lamps can likewise be used. Without restricting the generality, a structure is assumed in which the supplied light is collected by a collector and focused via a diaphragm and a downstream lens system on the object plane. The lens system can be composed of a fixed and a movable lens, the movable lens being movable in axial direction relative to the fixed lens. As a result thereof, the illumination intercept length can be varied.

With respect to the above-mentioned embodiment of an illuminating unit which is at least partly tiltable about an axis, it is useful with respect to the mentioned structure of the same to not design the entire illuminating unit tiltably but only a part thereof which is substantially formed by the mentioned diaphragm and the mentioned lens system. This part can easily be separated from the collector and the light source. The mentioned further deflector element (deflecting mirror) is in this case, as already mentioned, usually superfluous.

For constructional, optical and ergonomic reasons the use of the present invention is particularly suitable in a microscope having a "lying" zoom system (see the explanations made at the beginning). For this purpose, a zoom system is arranged downstream of the main objective, as viewed from the object plane, a deflector element being arranged between the zoom system and the main objective, which element deflects the viewing beam path coming from the main objective into a first horizontal plane in which the longitudinal axis of the zoom system lies. Below the zoom system, i.e. on its object-sided side, the illuminating unit of the microscope can then be arranged axially parallel. As a result thereof, one obtains a structure having a low overall height in vertical direction. Usually, the microscope has a tube and at least one eyepiece, in the case of a stereomicroscope a binocular tube, which are or, respectively, is arranged downstream of the zoom system. However, it shall also be noted here that between the magnification changer (zoom system) and the tube an output (optical and mechanical) can be present for documentation, to which output, for example, a camera can be connected. Via optical deflector means, the viewing beam path reaches from the mentioned first horizontal plane into a second horizontal plane which extends parallel thereto and in which optical add-on components and/or the tube are arranged. By means of this folding of the viewing beam path a microscope structure having a low overall height is guaranteed and in addition manifold possibilities of a coupling-out, for example, given a surgical microscope for assistant's viewing are created.

The present invention and its advantages shall be explained in more detail in the following on the basis of an embodiment illustrated in the enclosed drawing.

BRIEF DESCRIPTION OF THE DRAWINGS

FIG. 3 schematically shows the essential components of the invention used for illumination centering given a small working distance of the microscope.

DETAILED DESCRIPTION OF THE DRAWINGS

Figure 1:
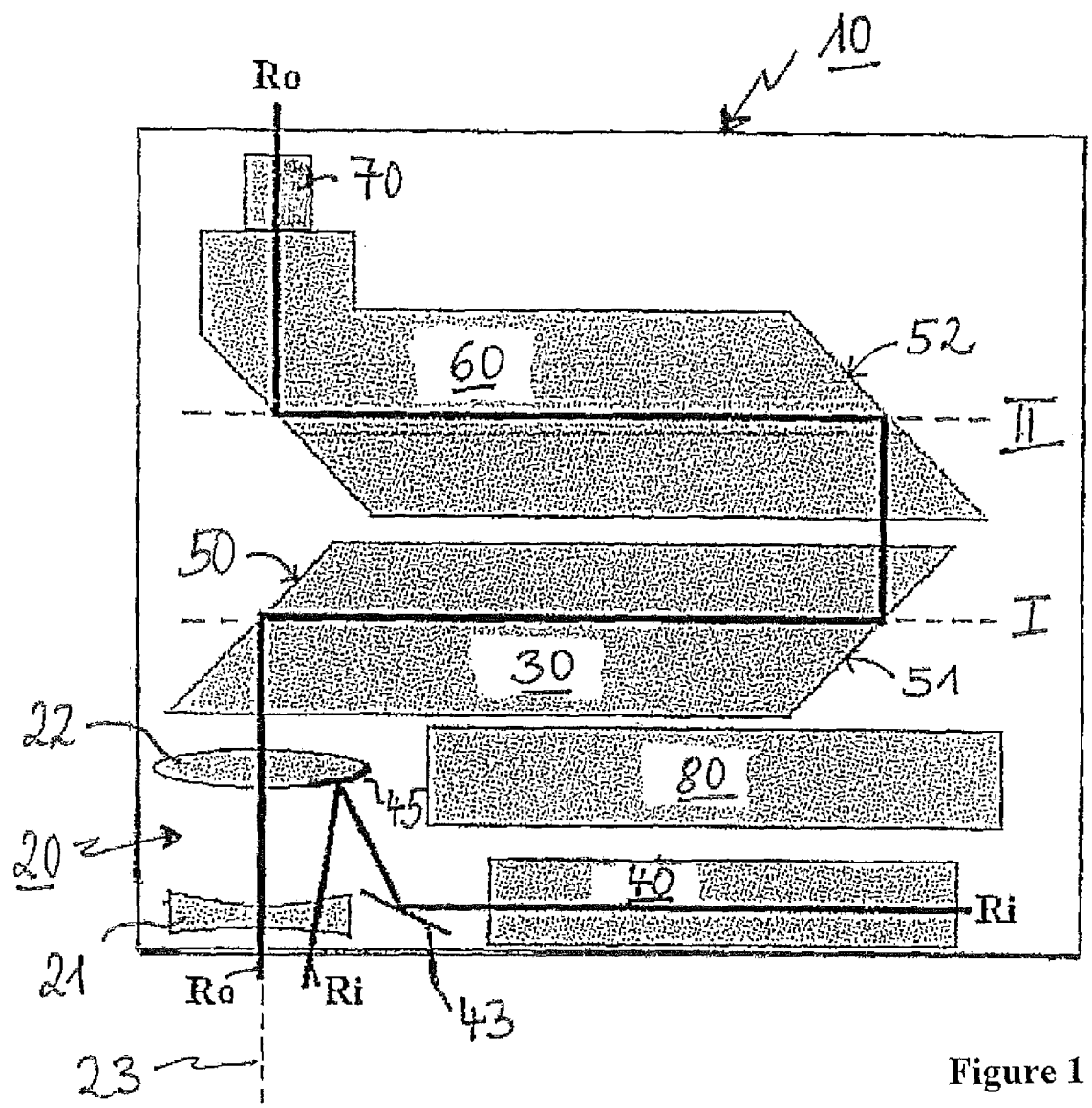
FIG. 1 schematically shows the structure of a microscope in which the invention can preferably be used.
Figure 1:

FIG. 1 very schematically shows the basic structure of a microscope 10, here designed as a surgical stereomicroscope, for a better illustration only the viewing axis $R_o$ being illustrated instead of the two viewing beam paths. Such surgical microscopes often have an additional pair of viewing beam paths for assistant's viewing. Microscopes of this type are known per se and therefore are not to be explained in more detail here. In this connection, reference is made to the stereomicroscope described in the already mentioned EP 1 424 582 B1 in which, as in the present case, a "lying" zoom system 30 is realized.

The surgical microscope 10 comprises a main objective 20 which is designed as a multi-focus (or variable focus lens), i.e. represents a lens having a variable focal length. The main objective 20 defines an optical axis 23 which is perpendicular to an object plane 100. By varying the focal length of the main objective 20, focusing on the respective object plane 100 can be effected. In FIG. 1, the multi-focus is illustrated by means of two lens assemblies 21 and 22, reference being made to the other possibilities of realizing a multi-focus mentioned at the beginning. Without restricting the generality, a structure is assumed in the following in which a lens assembly 22 having a positive focal length is movably mounted along the optical axis 23, whereas a second lens assembly 21 having a negative focal length is fixedly mounted in the main objective 20.

The viewing beam paths run parallel to the shown optical axis 23 and lie, for example, either in the drawing plane or in a plane perpendicular to the drawing plane and including the optical axis 23. For deflecting the viewing beam paths a first deflector element 50 is arranged in the beam path and deflects the viewing beam paths from a substantially vertical direction into a substantially horizontal direction into the "lying" zoom system 30. The zoom system 30 is arranged with its longitudinal axis in a first horizontal plane I. Instead of a zoom system 30 which serves for the continuous magnification of the object image a discretely operating magnification changer can likewise be provided. By means of further deflector elements 51 and 52, the viewing beam path is directed into a second horizontal plane II. Here, the tube 60 is arranged, which directs the illuminating beam path into at least one eyepiece 70 through which an observer can view the microscope image. In the case of stereomicroscopes, the eyepieces 70 and the tube 60 are usually combined to a binocular tube. The principle structure of the described microscope components such as main objective, zoom system, tube and eyepieces is common knowledge for the person skilled in the art. In the beam path illustrated in FIG. 1, optical add-on components such as filters, image inverters, components for extending the optical path length, optical beam splitters for assistant's viewing, reflecting-in and reflecting-out devices (for example data reflecting-in devices) etc. can be arranged. Finally, between the zoom system 30 and the actual tube 60 an output (optical/mechanical) for documentation (camera, video, etc.) can be present.

An illuminating unit 40 which can be arranged ergonomically favorable with its longitudinal axis substantially horizontally below the zoom system 30 serves for the illumination of the object. What is illustrated here is a fiber illumination via an optical fiber. However, a direct halogen, xenon or LED illumination can likewise be used. The illuminating beam path generated by the illuminating unit 40 and illustrated by means of its illuminating axis $R_i$ is directed by means of illumination deflector means 43 and 45 in the direction of the object plane 100. As can be taken from FIG. 1 and FIGS. 3 and 4 still to be explained, the illuminating beam path can be guided via a part of the main objective 20 (here via the lens assembly 21) or, respectively, outside the main objective 20 of the microscope 10. Since in any case, the illuminating beam path is not completely guided through the main objective 20, given a focal length variation of the main objective 20 which results in a shift of the object plane 100 in vertical direction, the illuminating beam path and thus its axis $R_i$ has to be tracked (re-adjusted) for an optimal illumination. The inventive type of this tracking of the illumination will be explained in more detail on the basis of the following figures.

With respect to the microscope structure illustrated in FIG. 1, it is added that the construction of the illumination deflector means 43 and 45, which is still to be explained in more detail, makes it possible to create enough space below the zoom system 30, for example, for the arrangement of the zoom motor 80 or other components necessary or useful for the operation of the microscope 10. Should the space occupied by the zoom motor 80 in the present example not be required then a different structure of an illuminating unit 40, in particular without the additional deflector element 43 (deflecting mirror) can be realized. In this connection, a partly tiltably designed illuminating unit 40 can likewise be considered, which will be dealt with later on.

Figure 2:
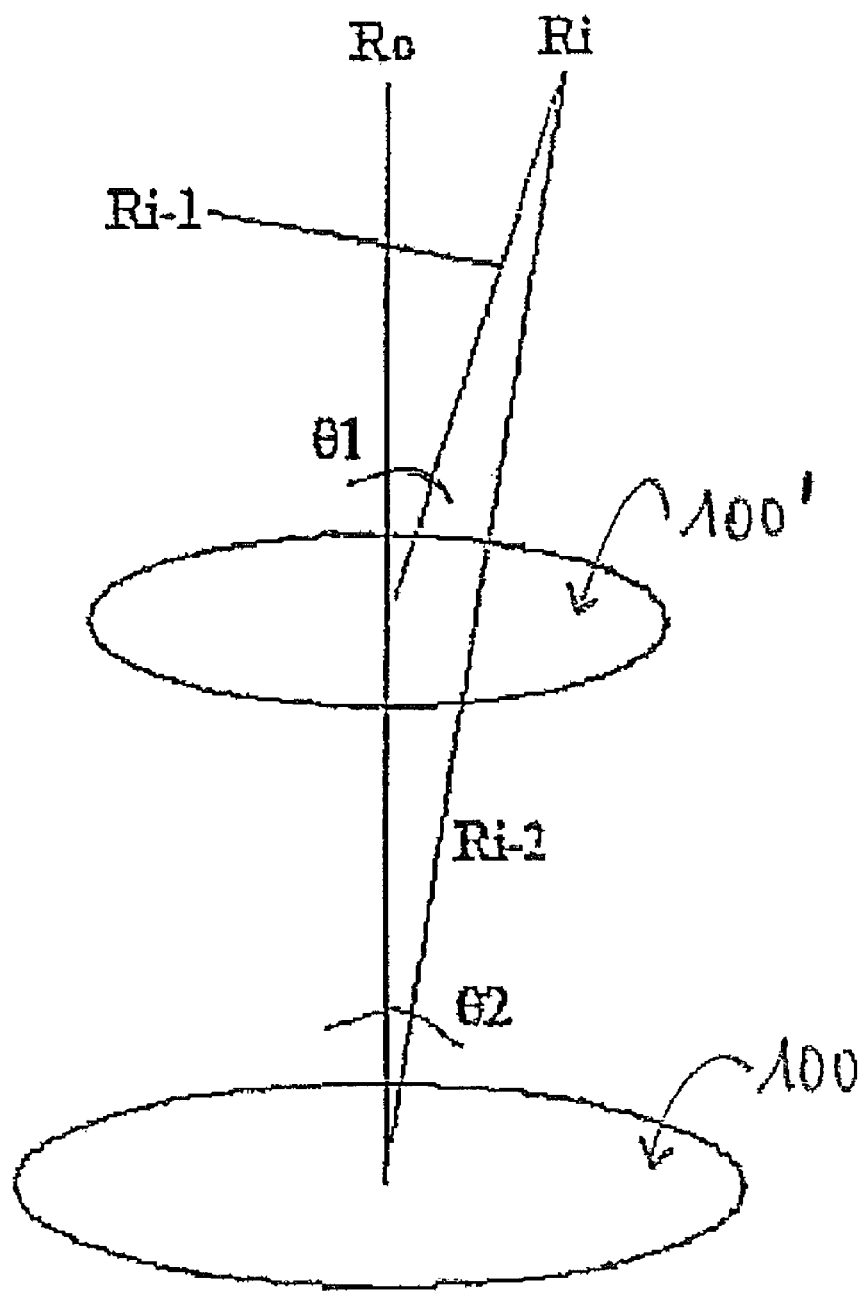
FIG. 2 is a graphic illustration of the sequence of illumination centering given a focal length variation of the main objective.

As can be taken from a combination of FIGS. 1 and 2, the axis $R_i$ of the illuminating beam path encloses the angle $\theta$ with the axis $R_o$ of the viewing beam path.

FIG. 2 illustrates the required change of the mentioned angle $\theta$ given a focal length variation of the main objective 20 or given a variation in the working distance between this main objective 20 and the object plane 100. With decreasing focal length of the main objective 20 and thus decreasing working distance, the angle $\theta$ is increased. FIG. 2 shows two extreme positions, for example maximum and minimum working distance, the axis $R_{i2}$ of the illuminating beam path being directed onto the focus of the main objective 20 given a greater working distance. Here, the angle $\theta_2$ results. Given a smaller working distance, the angle $\theta$ has to be increased, until, for example, the angle $\theta_1$ with the associated illuminating axis $R_{i1}$ is reached. From the maximum and the minimum working distance of the main objective 20, thus a range for the angle $\theta$ can be given which is to be tracked given a change in the working distance in order to achieve a centered illumination. The object planes assigned to the angles $\theta_1$ and $\theta_2$ are designated with 100' and 100 in FIG. 2.

Figure 4:
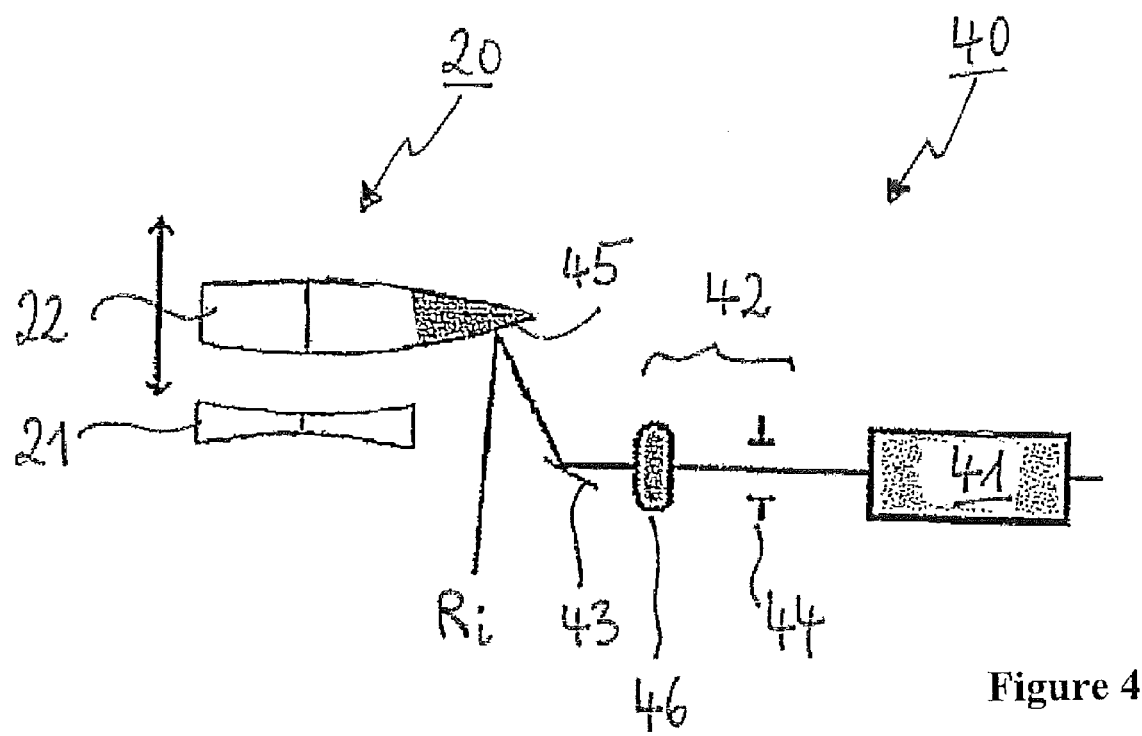
FIG. 4 schematically shows the essential components of the invention used for illumination centering given a large working distance of the microscope.
Figure 4:
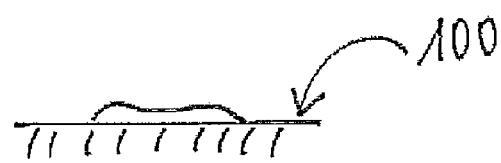

FIG. 3 and FIG. 4 show in the form of a detailed cutout (see FIG. 1 with respect hereto) an embodiment of the invention for illumination centering given a change in the working distance, in FIG. 3 the main objective being focused, for example, on the plane 100' (see FIG. 2), whereas in FIG. 4 the main objective 20 being focused on the object plane 100 (see FIG. 2).

In FIG. 3, the structure of an illuminating unit 40 is illustrated, as can be used for example in the present invention. 41 designates a collector (here with the light source) which collects the light from the light source and images the same via the diaphragm 44 and the illuminating lens assembly 46 into the object plane 100'. The diaphragm 44 concerned is, for example, an iris diaphragm in the function of a field diaphragm with variable diameter. Without restricting the generality, a structure is assumed as already outlined in FIG. 1, namely with an illumination deflector element 43 (deflecting mirror) which can be designed as a plane mirror but also as a spherical mirror. The illuminating lens assembly 46 can represent a single lens or (as usual) a combination of lenses. In particular, an illuminating zoom is often used for this purpose, in which two (or more) lens groups are movable relative to one another in order to vary the illumination intercept length.

The illuminating beam path is, after reflection at the deflector element 43, directed in the direction of the movable lens assembly 22 of the main objective 20 of the microscope 10 (see FIG. 1), wherein according to the invention the illuminating beam path is reflected at this lens assembly and is directed into the object plane 100'. For this purpose, the periphery of the lens assembly 22 is formed as a deflector element 45. This deflector element 45 can, for example, be a (plane or spherically shaped) deflecting mirror which is firmly connected to the lens assembly 22 or can be a lens surface of the lens assembly 22 that has been made reflective in part. In another embodiment the lens assembly 22 and the deflector element 45 can be cemented lens members or a lens having a freeform surface. In particular, this can have the advantage that the curvature of the deflector element 45 (reflective part of the lens assembly) can be different from the curvature of the actual lens assembly 22 (image-forming part).

As can be taken from FIG. 3, the illuminating beam path is guided outside the main objective 20. Of course, embodiments can likewise be realized in which the illuminating beam path can be guided through the (fixed) lens assembly 21 (see FIG. 1).

FIG. 3 shows an illustration of the positions of the two lens assemblies 21 and 22 for a smaller working distance which is achieved by a great distance between the two lens assemblies 21 and 22 when the two lens assemblies 21 and 22 have focal lengths with different signs. In the specific example the fixed lens assembly 21 facing the object is a lens assembly having a negative focal length, and the movable lens assembly 22 facing away from the object is one having a positive focal length. Once again, reference is made here to the already mentioned possibilities for the realization of a multi-focus.

The transition to large working distances is illustrated in FIG. 4. For this purpose, the distance between the lens assemblies 21 and 22 with respect to one another is reduced by moving the movable lens assembly 22 along the optical axis 23 in the direction of the fixed lens assembly 21. As results from a comparison between FIG. 3 and FIG. 4, the illumination centering is automatically tracked without the deflector element 43 having to change its position. The required change in the angle θ results automatically in that the illuminating beam path (axis $R_i$) is reflected at another position of the reflective lens surface given a changed position of the lens assembly 22 so that the angle of reflection at the lens assembly 22 and thus also the illumination angle θ automatically changes.

As already mentioned, a part of the illuminating unit 40 can be tiltably designed so that in this way the illuminating beam path tracks a movement of the lens assembly 22 of the main objective 20. In this case, the deflector element 43 can be omitted. It is expedient to select a part 42 of the illuminating unit 40 which substantially consists of the diaphragm 44 and the illumination lens assembly 46 and to define the rotary axis about which the tilting of the part 42 of the illuminating unit 40 takes place such that it is perpendicular to the drawing plane and in the center of the diaphragm 44.

If necessary, further parameters of the illuminating unit can be optically changed in order to achieve an optimal coupling of the illuminated field to the field of view with respect to position, size and brightness. As an example, a change in the intercept length of the lens assembly 46 is mentioned, as a result whereof the illumination intercept length can be adapted or tracked to the viewing intercept length. As a result thereof, the intensity in the illuminated field is likewise changed and can thus be coupled optimally with the varied focal length of the main objective 20. Further, the opening diameter of a field diaphragm 44 can be coupled with a change in the working distance. As a result, the size of the illuminated field can be optimally adapted to the size of the field of view. For the purposes mentioned, the control unit can be provided, which, on the one hand, measures a focal length variation of the main objective 20 and, on the other hand, is connected to corresponding adjustment devices for adjusting the lens assembly 46 and/or the opening diameter of the diaphragm 44.

Figure 5:
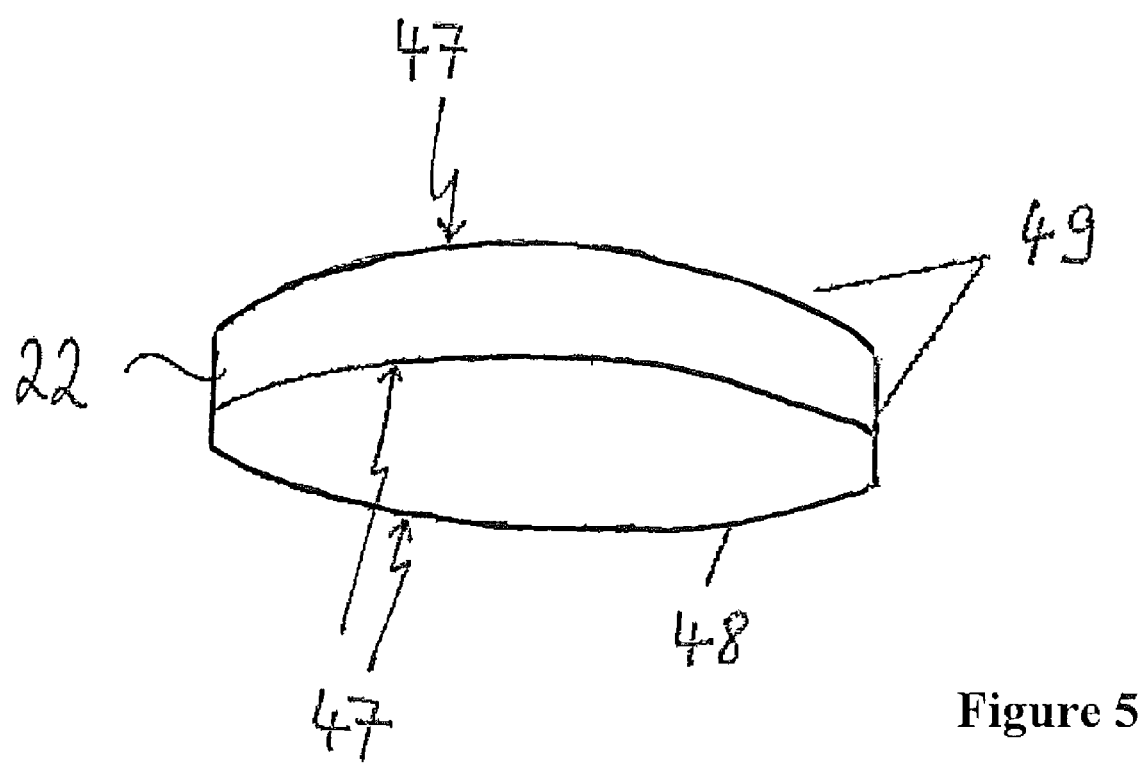
FIG. 5 shows a longitudinal section of a lens assembly of the main objective of the microscope that has partially been made reflective.

With reference to FIG. 5, the possibilities shall be explained as to which specific part of a lens surface 47 can be made reflective. Again, and without restricting the generality, it is assumed that a lens assembly 22 having a positive focal length is movably mounted for changing the focal length of the main objective 20. In particular when working with small working distances, a multi-focus structure is used in which the lens assembly 22 having a positive focal length can be moved relative to a lens assembly 21 having a negative focal length in order to vary the working distance. Without restricting the generality, it is again assumed that the second lens assembly having a negative focal length is stationarily mounted in the main objective 20. As can be taken from FIGS. 3 and 4, with this multi-focus, the working distance increases with decreasing distance between the two lens assemblies 21, 22 so that the angle of reflection of the illuminating beam path (axis $R_i$) has to become greater with decreasing distance between the lens assemblies in order to adapt the illumination centering optimally to the changed focal length of the main objective. This necessary change in the angle of reflection can automatically be achieved in that a part of the convex lens surface 48, i.e. a part of the lens surface 48 facing the object plane, is made reflective.

A structure of a multi-focus lens is also known in which substantially two lens assemblies having a positive focal length are movably mounted on an optical axis. In this case, the working distance of the main objective increases with increasing distance between the two lens assemblies. Thus, the relationships are just the other way around compared to the case already described above. Therefore, in this case it is expedient to make at least part of a concave lens surface 49 of the lens assembly 22 reflective. FIG. 5 shows a possible structure of a lens assembly which altogether has a positive focal length. The lens assembly concerned is a two-member lens component. Here, two concave surfaces 49 are available for being made reflective.

The embodiments described herein shall merely illustrate the invention and are suitable for providing the person skilled in the art with combination possibilities that have not been explicitly discussed herein, which are, however, within the scope of the invention. The features of the invention as discussed herein, can thus not only be realized in the combination as illustrated herein but also in other combinations or, as far as technically useful, alone without leaving the scope of the invention.

LIST OF REFERENCE NUMERALS 10 microscope
20 main objective, multi-focus, variable focus lens
21 fixed lens assembly
22 movable lens assembly
23 optical axis
30 zoom system
40 illuminating unit
41 collector and light source
42 tiltable part of the illuminating unit
43 illumination deflector means, additional deflector element, deflecting mirror
44 diaphragm, iris diaphragm
45 illumination deflector means, deflector element
46 lens assembly
47 lens surface
48 convex lens surface
49 concave lens surface
50 deflector element
51 deflector element
52 deflector element
60 tube
70 eyepiece
80 zoom motor
100, 100' object plane
I first horizontal plane
II second horizontal plane
$R_o$ viewing axis
$R_i$ illuminating axis
$\theta$ angle $R_i$ to $R_o$

The invention claimed is:

1. A microscope comprising:
   a main objective having a movable lens assembly; and
   an illuminating unit with illumination deflector means for deflecting an illuminating beam path in such a manner that an illuminating beam path is generated that is directed onto an object plane; wherein
   the movable lens assembly is movable in a direction of the optical axis of the main objective for a focal length change;
   the position of the illumination deflector means is adjustable for centering the illumination for various focal lengths of the main objective;
   at least a part of the illumination deflector means is integrated into the movable lens assembly of the main objective; and
   the part of the illumination deflector means integrated into the lens assembly of the main objective represents an at least partially reflecting lens surface of the movable lens assembly.

2. The microscope according to claim 1, wherein the part of the illumination deflector means integrated into the lens assembly of the main objective represents a deflector element firmly connected to the movable lens assembly.

3. The microscope according to claim 2, wherein the deflector element has a plane reflecting surface.

4. The microscope according to claim 2, wherein the deflector element has a spherical reflecting surface.

5. The microscope according to claim 2, wherein the deflector element has a freeform reflecting surface.

6. The microscope according to claim 1, wherein the illumination deflector means have a further deflector element that optically interacts with the part of the illumination deflector means integrated into the lens assembly of the main objective.

7. The microscope according to claim 6, wherein the main objective has two lens assemblies having focal lengths with different signs for focal length variation, at least the lens assembly having a positive focal length being movably mounted and the part of the illumination deflector means integrated into this lens assembly represents a convex lens surface of this lens assembly that has been made reflective at least in part.

8. The microscope according to claim 6, wherein the main objective has two lens assemblies having focal lengths with positive sign for focal length variation, at least one of the lens assemblies being movably mounted and the part of the illumination deflector means integrated into this lens assembly represents a concave lens surface of this lens assembly that has been made reflective at least in part.

9. The microscope according to claim 1, wherein the main objective has two lens assemblies having focal lengths with different signs for focal length variation, at least the lens assembly having a positive focal length being movably mounted and the part of the illumination deflector means integrated into this lens assembly represents a convex lens surface of this lens assembly that has been made reflective at least in part.

10. The microscope according to claim 1, wherein the main objective has two lens assemblies having focal lengths with positive sign for focal length variation, at least one of the lens assemblies being movably mounted and the part of the illumination deflector means integrated into this lens assembly represents a concave lens surface of this lens assembly that has been made reflective at least in part.

11. The microscope according to claim 1, wherein the lens curvature on the reflecting surface area of the lens assembly differs from the lens curvature on the non-reflecting surface area of the lens assembly.

12. The microscope according to claim 1, wherein the illuminating beam path generated by the illumination deflector means extends through at least a part of the main objective.

13. The microscope according to claim 1, wherein at least a part of the illuminating unit is designed such that the illuminating beam path generated by the illuminating unit tracks a movement of the part of the illumination deflector means integrated into the movable lens assembly of the main objective.

14. The microscope according to claim 13, wherein at least a part of the illuminating unit is mounted in such a manner that it tilts around an axis that is substantially perpendicular to a plane extending between the optical axis of the main objective and the axis of the illuminating beam path.

15. The microscope according to claim 1, wherein the microscope comprises a zoom system arranged downstream of the main objective as viewed from the object plane.

16. The microscope according to claim 15, wherein a deflector element is arranged between the zoom system and the main objective, said deflector element directing the viewing beam path coming from the main objective into a first horizontal plane in that the longitudinal axis of the zoom system lies.

17. The microscope according to claim 1, wherein the microscope comprises a tube and an eyepiece that are arranged downstream of the zoom system.

18. The microscope according to claim 17, wherein a deflector element is arranged between the zoom system and the main objective, said deflector element directing the viewing beam path coming from the main objective into a first horizontal plane in that the longitudinal axis of the zoom system lies;

a second horizontal plane extends substantially parallel to the first horizontal plane; and at least the tube is arranged in such a manner that its longitudinal axis extends in the second horizontal plane.

19. The microscope according to claim 1, wherein the microscope is designed as a stereomicroscope, in particular as a surgical microscope.

* * * * *